US006290663B1

(12) United States Patent
Darcey

(10) Patent No.: US 6,290,663 B1
(45) Date of Patent: Sep. 18, 2001

(54) MEDICAL BANDAGING PRODUCT WITH TUBULAR-KNITTED SUBSTRATE

(75) Inventor: Thomas D. Darcey, Mooresville, NC (US)

(73) Assignee: Smith & Nephew, Inc., Charlotte, NC (US)

( * ) Notice: Subject to any disclaimer, the term of this patent is extended or adjusted under 35 U.S.C. 154(b) by 0 days.

(21) Appl. No.: 09/443,200

(22) Filed: Nov. 18, 1999

(51) Int. Cl.$^7$ ............................................ A61F 5/00
(52) U.S. Cl. ............................ 602/8; 602/5; 602/6
(58) Field of Search .................... 602/5, 6, 7, 8, 602/10, 11

(56) References Cited

U.S. PATENT DOCUMENTS

| | | |
|---|---|---|
| 4,668,563 | 5/1987 | Buese et al. . |
| 4,984,566 | 1/1991 | Sekine et al. . |
| 5,003,970 * | 4/1991 | Parket et al. ............................ 602/8 |
| 5,403,267 | 4/1995 | Pearce et al. . |
| 5,461,885 | 10/1995 | Yokoyama et al. . |
| 5,514,080 | 5/1996 | Blott et al. . |

* cited by examiner

Primary Examiner—Kim M. Lewis

(74) Attorney, Agent, or Firm—Adams, Schwartz & Evans, P.A.

(57) ABSTRACT

An elongate medical bandaging product for being dispensed in lengths suitable for a given medical use, including an elongate sleeve of a predetermined length formed of a moisture-impervious material and sealable to prevent entry of moisture, and an elongate medical material having substantially the same predetermined length as the elongate sleeve and positioned in a continuous layer which coextends within the sleeve in substantially moisture-free conditions and sealed therein against moisture until use. The medical material includes a tubular substrate having a pair of opposed, major surfaces defining folded side edges extending along the length of the elongate sleeve and characterized by being substantially free of cut fibrous ends, a reactive system impregnated into or coated onto the substrate, the system remaining stable when maintained in substantially moisture-free conditions and hardening upon exposure to sufficient moisture to form a rigid, self supporting structure, and a soft, flexible protective wrapping enclosing the substrate along its length to provide a cushioning barrier between the substrate and the skin of a patient when the material is in use. A desired length of the medical material is therefore removable from the length of bandaging product by severing the medical material and the sleeve at a desired point without removing additional excess medical material from the sleeve.

31 Claims, 7 Drawing Sheets

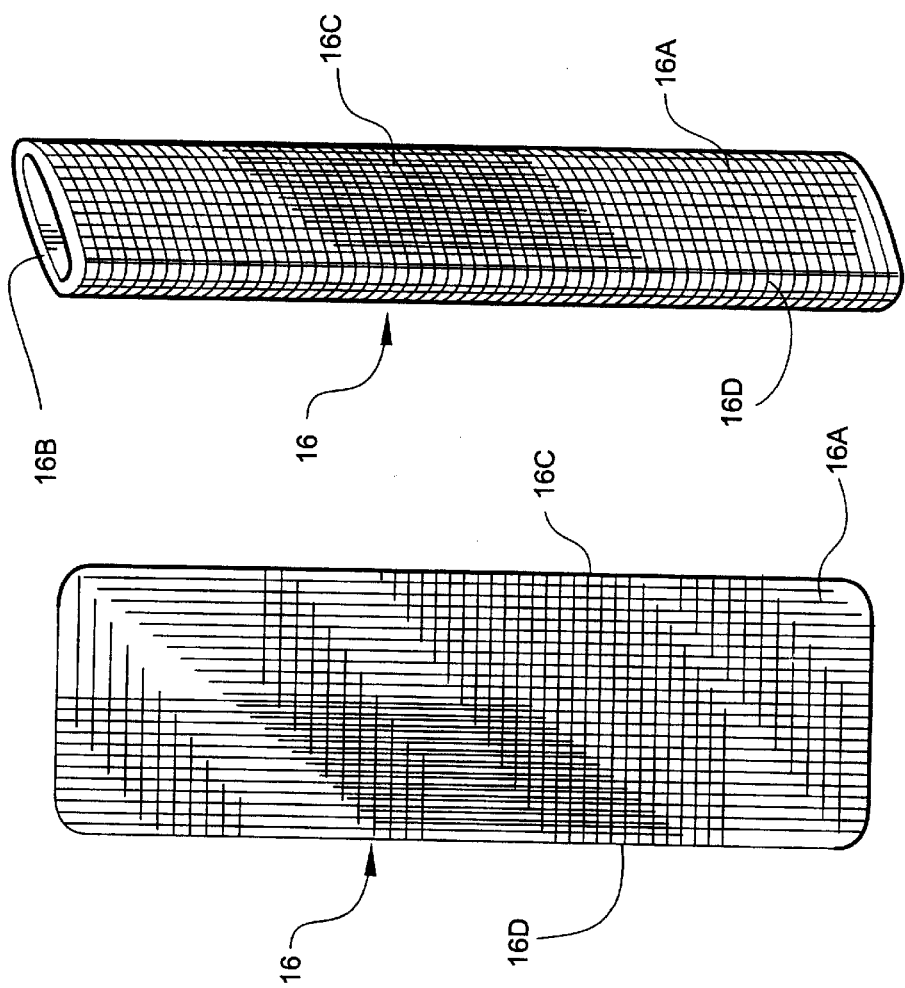
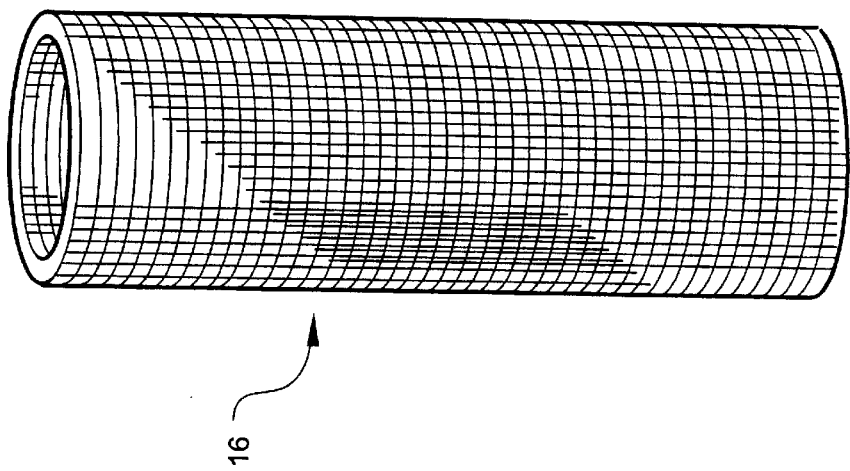

MEDICAL BANDAGING PRODUCT WITH TUBULAR-KNITTED SUBSTRATE

TECHNICAL FIELD AND BACKGROUND OF THE INVENTION

This invention relates to a relates generally to the field of orthopedic medicine and more specifically to the design of an improved medical bandage formed of a moisture-curable synthetic resin material and containers for storing and dispensing such a roll form bandaging product.

Medical bandages for use in the treatment of injuries, such as broken bones requiring immobilization of a body member, are generally formed from a strip of fabric or scrim material impregnated with a substance which hardens into a rigid structure after the strip has been wrapped around the body member. The hardening substance traditionally used in carrying out this procedure is plaster-of-paris.

Conventional practice has been to fabricate a cast or splint upon an injured limb by initially applying to the limb a protective covering of a cotton fabric or the like and then overwrapping the covering and limb with a woven cloth impregnated with plaster-of-paris which has been wetted by dipping in water immediately prior to application. This practice is still in widespread use but possesses several significant disadvantages. For example, the above-described application procedure is messy and time-consuming. Several components are required and considerable skill is necessary.

In order to alleviate the above-recited disadvantages of the conventional application procedure for plaster-of-paris casts and splints, unitary splinting materials have been devised and are disclosed in, for example, U.S. Pat. Nos. 3,900,024, 3,923,049, and 4,235,228. All of these patents describe a padding material with a plurality of layers of plaster-of-paris impregnated cloth. Such unitary splinting materials are not as messy and can be applied more quickly but still suffer from a number of disadvantages inherent in plaster-of-paris cast materials. All plaster-of-paris splints have a relatively low strength to weight ratio which results in a finished splint which is very heavy and bulky. Plaster-of-paris splints are slow to harden, requiring 24 to 72 hours to reach maximum strength. Since plaster-of-paris breaks down in water, bathing and showering are difficult. Even if wetting due to these causes can be avoided, perspiration over an extended period of time can break down the plaster-of-paris and create a significant problem with odor and itching.

A significant advance in the art of casting and splinting is disclosed in U.S. Pat. Nos. 4,411,262 and 4,502,479. The casting materials disclosed in these patents comprise a flexible fabric impregnated with a moisture-curing resin enclosed in a moisture-free, moisture-impervious package. Compared to plaster-of-paris, these products are extremely lightweight, have a very high strength to weight ratio and can be made relatively porous, permitting a flow of air through the casting material. Prior art moisture-curing systems include a package within which is contained a plurality of layers of fabric, such as fiberglass, impregnated with a moisture-curing resin. No provision is made for re-closing the package, so that the entire material must be very quickly used after removal from the package since such moisture-curing resins will cure in a relatively short period of time due merely to contact with atmospheric moisture.

This technology has permitted the development of lightweight, easy to apply splints, as exemplified in U.S. Pat. Nos. 4,770,299, 4,869,046, 4,899,738, 5,003,970 and 5,415,622. Such splints now dominate the market for medical splints.

From the above discussion, it can be seen that both the conventional plaster-of-paris casting method and the more recent moisture-curable resin casting method possess both advantages and disadvantages. On the one hand, plaster-of-paris casts are bulky, heavy and difficult to apply whereas moisture-curable resin casts are lightweight, durable and relatively easy to apply. Plaster-of-paris can be very easily stored and used as needed since it has a relatively long shelf life so long as it is not completely wetted. On the other hand, the moisture-curable resins are very sensitive to the presence of even minute amounts of moisture which requires that either the materials be packaged in a wide variety of different shapes and sizes or unused portions be discarded, generating a substantial amount of waste and increasing the effective cost of the product. This invention combines the advantages of both plaster-of-paris and moisture-curable resin systems while avoiding their respective disadvantages. This is accomplished by providing a unitary splinting system with improved strength and convenience. A unitary system is provided with the use of moisture-curing resin casting materials, together with a moisture-impervious package with means for resealing the package against entry of moisture after a desired length of bandaging product has been removed for use. In this manner, hardening of the bandaging product remaining in the moisture-impervious package is prevented thereby increasing the cost effectiveness of the system substantially.

However, there are still some disadvantages to the synthetic splinting system described above. In particular, woven fiberglass fabric is typically used as the substrate which carries the moisture-curable resin. The substrate is formed of several layers of fabric, for example, warp knitted fabric, which have been cut into strips of the correct length and width. The process of cutting the fiberglass fabric to the correct size leaves cut fibers and yarns projecting outwardly from the sides and the ends of the splinting material. As manufactured, this fabric is relatively soft and flexible. Moreover, the substrate is fully enclosed with the surrounding padding material. After curing, however, the cut fibers and yarns become hard and needle-like. These projections can project through the thickness of the padding material into contact with the skin of the patient causing skin-sticks, cuts, irritation and itching. Similar problems can exist with substrates fabricated from woven or knitted thermoplastic yarns which must be cut to the proper length and width.

Moreover, the splint manufacturing process utilizing flat fabric is relatively labor intensive, since the woven or knitted fabric must be cut to the proper length and width and overlaid with other layers of fabric, usually 4 to 8, to produce the substrate. In order to properly form the substrate, the overlaid layers must be carefully aligned so that the width and thickness are even. In instances where the multiple overlaid layers are stitched together, even more labor is required.

More recently, non-woven fabrics have been introduced into the splinting field. Non-woven fabrics do provide a smoother edge that do woven or knitted fabrics. However, non-woven fabrics are thicker, inhibiting the ability of the product to conform to the extremities as easily as does the woven or knitted fabric substrates. The greater thickness also makes the it difficult to evenly impregnate or coat the substrate with resin.

SUMMARY OF THE INVENTION

Therefore, it is an object of the invention to provide a medical bandaging product in roll form with a moisture-curable resin which hardens the material upon exposure to moisture to form a rigid, self-supporting structure.

It is another object of the invention to provide a medical bandaging product which can be dispensed in any desired length while preventing hardening of the remaining material until use is desired.

It is another object of the invention to provide a unitary medical bandaging product which includes a wrapping to provide a cushion against the skin of a patient.

It is an object of the invention to provide a bandaging product which utilizes a tubular knitted or woven fabric structure as a bandage substrate.

It is an object of the invention to provide a bandaging product which is dispensed from a protective container.

It is another object of the invention to provide a bandaging product which has a tubular substrate which is uniform in dimension without the requirement for additional fabrication steps after formation of the tube.

It is another object of the invention to provide a bandaging product which has a substrate without cut fibers or yarns extending from the sides of the substrate.

These and other objects and advantages of the present invention are achieved in the preferred embodiment disclosed below by providing an elongate medical bandaging product for being dispensed in lengths suitable for a given medical use, comprising an elongate sleeve of a predetermined length formed of a moisture-impervious material and sealable to prevent entry of moisture, and an elongate medical material having substantially the same predetermined length as the elongate sleeve and positioned in a continuous layer which coextends within the sleeve in substantially moisture-free conditions and sealed therein against moisture until use. The medical material comprises a tubular substrate having a pair of opposed, major surfaces defining folded side edges extending along the length of the elongate sleeve and characterized by being substantially free of cut fibrous ends, a reactive system impregnated into or coated onto the substrate, the system remaining stable when maintained in substantially moisture-free conditions and hardening upon exposure to sufficient moisture to form a rigid, self supporting structure, and a soft, flexible protective wrapping enclosing the substrate along its length to provide a cushioning barrier between the substrate and the skin of a patient when the material is in use. A desired length of the medical material is therefore removable from the length of bandaging product by severing the medical material and the sleeve at a desired point without removing additional excess medical material from the sleeve. The sleeve and medical material form a continuum of elongate bandaging product whereby the sleeve is sealable against entry of moisture after a desired length of the medical material has been dispensed for use to prevent hardening of the substrate remaining in the sleeve.

According to one preferred embodiment of the invention, the tubular substrate comprises a knitted fabric.

According to another preferred embodiment of the invention, the tubular substrate comprises a seamless knitted fabric knitted on a circular knitting machine.

According to yet another preferred embodiment of the invention, the tubular substrate comprises a knitted fabric knitted on a flat knitting machine having a seam therein which binds two side edges of the knitted fabric together to form a tube.

According to yet another preferred embodiment of the invention, the sleeve comprises a aluminum foil laminate having an outer tear resistant layer, a central aluminum foil layer and an inner heat sealable plastic layer.

According to yet another preferred embodiment of the invention, the tubular substrate is formed of fibers selected from the group consisting of fiberglass and synthetic thermoplastic fibers.

According to yet another preferred embodiment of the invention, the protective wrapping enclosing the substrate comprises a fibrous nonwoven cushion.

Preferably, the protective wrapping enclosing the substrate comprises a nonwoven polypropylene tube.

According to yet another preferred embodiment of the invention, the reactive system comprises a blended polyisocyanate, polyol, catalyst and stabilizer.

According to yet another preferred embodiment of the invention, the sleeve is formed into a coil.

According to yet another preferred embodiment of the invention, a dispensing carton is provided within which the coil of medical bandaging product is contained.

According to one preferred embodiment of the invention, an elongate medical material is adapted for being maintained in substantially moisture-free conditions until use. The medical bandage comprises a tubular substrate defining a pair of opposed major surfaces defining folded side edges extending along the length of the substrate and characterized by being substantially free of cut fibrous ends. A reactive system is impregnated into or coated onto the substrate, the system remaining stable when maintained in substantially moisture-free conditions and hardening upon exposure to sufficient moisture to form a rigid, self supporting structure. A soft, flexible protective wrapping encloses the substrate along its length to provide a cushioning barrier between the substrate and the skin of a patient when the bandage is in use.

According to yet another preferred embodiment of the invention, the soft, flexible protective wrapping enclosing the substrate comprises is freely water and air permeable through the thickness thereof for providing a cushioning barrier between the substrate and the skin of a patient when the bandage is in use, and which permits the moisture-curable resin to be quickly and easily exposed to water through the thickness thereof.

According to yet another preferred embodiment of the invention, the soft, flexible, protective wrapping surrounds the substrate so that either of the enclosed major surfaces of the substrate may be placed adjacent the skin of the patient.

According to yet another preferred embodiment of the invention, an elongate medical bandaging product is provided for being dispensed in lengths suitable for a given medical use, and comprises an outer container formed of a moisture-impervious material and sealable to prevent entry of moisture, the container comprising an elongate product-dispensing sleeve having a moisture-proof sealable opening on one end and an enlarged product storage package communicating with the dispensing sleeve and an elongate medical material positioned in the container in substantially moisture-free conditions and sealed therein against moisture until use. The medical material comprises a tubular substrate having a pair of opposed, major surfaces defining folded side edges extending along the length of the elongate sleeve and characterized by being substantially free of cut fibrous ends; a reactive system impregnated into or coated onto the substrate, the system remaining stable when maintained in substantially moisture-free conditions and hardening upon exposure to sufficient moisture to form a rigid, self supporting structure, and a soft, flexible protective wrapping enclosing the substrate along its length to provide a cushioning barrier between the substrate and the skin of a patient when the material is in use. Closure means are provided for resealing the dispensing sleeve against entry of moisture after a predetermined length of the medical material has been dispensed for use to prevent hardening of the substrate remaining in the product container.

According to yet another preferred embodiment of the invention, the dispensing sleeve and the product storage package are integrally-formed.

According to yet another preferred embodiment of the invention, a protective carton is provided within which the product container is contained.

According to yet another preferred embodiment of the invention, the elongate medical material is coiled within the storage package with an end portion thereof positioned in the product-dispensing sleeve for selective dispensing of desired lengths thereof.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 6 is a perspective view of a length of tubular knitted substrate;

FIG. 7 is a side elevation of the tubular substrate in a flattened condition as it will be incorporated into the medical bandage;

FIG. 8 is a perspective view of the substrate shown in FIG. 7;

DESCRIPTION OF THE PREFERRED EMBODIMENT AND BEST MODE

Figure 1:
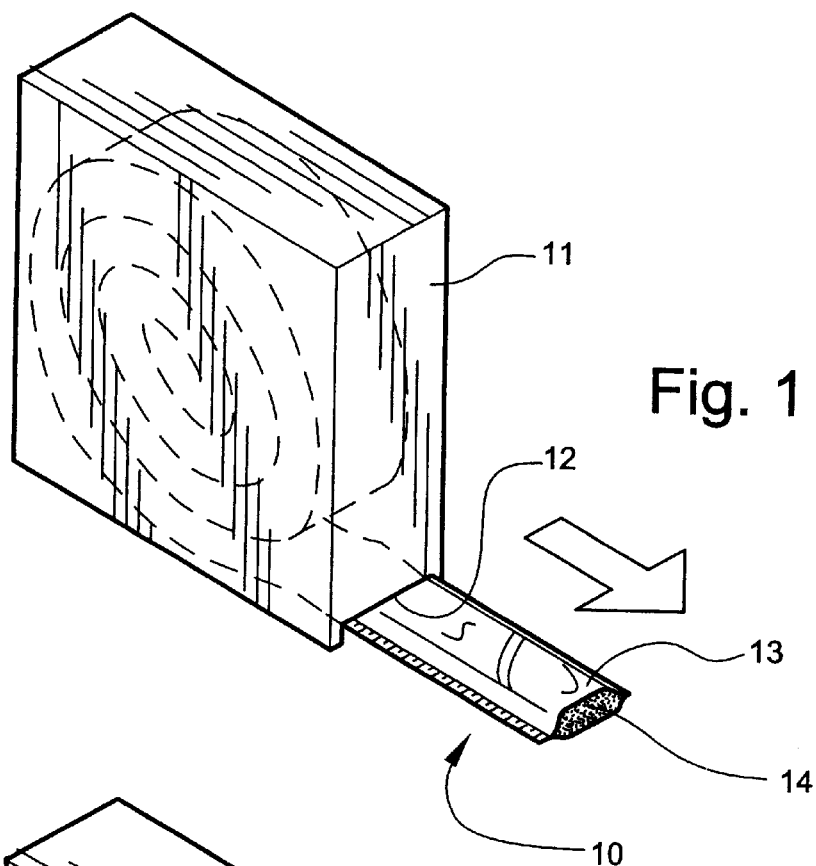
FIG. 1 is a perspective, schematic view showing the medical bandaging product being dispensed from a dispenser.

Referring now specifically to the drawings, a according to the present invention is illustrated in FIG. 1 and shown generally at reference numeral 10.

Referring now specifically to the drawings, a medical bandaging product according to the present invention is shown generally in FIG. 1 at 10. Bandaging product 10 may be sold in any convenient length, such as 24 feet, and is rolled into a coil and positioned in a suitable dispenser carton 11. Dispenser carton 11 is provided with a slot 12 at one lower corner through which bandaging product 10 extends.

Bandaging product 10 is comprised generally of an outer elongate sleeve 13 which is formed of a moisture-impervious material, such as two laminated elongate sheets placed in registration and heat sealed along its opposite sides to form a tube. The outer layer is formed of a tear-resistant plastic film. The middle layer comprises aluminum foil and acts as a moisture barrier. The inner layer is a plastic film having thermoplastic properties suitable for heat sealing the interior of sleeve 13 securely against moisture.

Sleeve 13 is preferably heat-sealed along opposite, parallel extending sides to form an elongate tube. An elongate medical material 14, described in detail below, is positioned within sleeve 13 and is maintained in substantially moisture-free conditions until dispensed.

Figure 2:
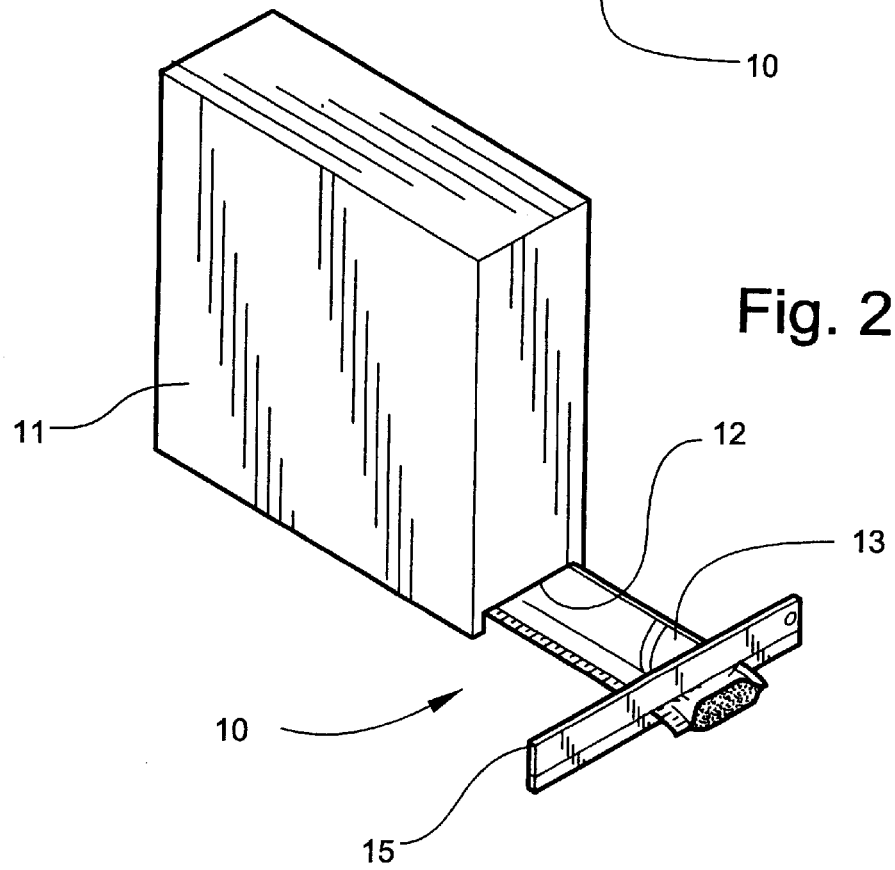
FIG. 2 is a view similar to FIG. 1, showing the unused portion of the medical bandaging product being resealed to prevent entry of moisture.

As is shown in FIG. 2, the end of sleeve 13 is sealed with sealing means, such as a scissor-type clamp 15.

Other types of sealing mechanisms are possible such as, for example, a soft, conformable gasketing device with spring loaded compression, moisture-proof tape, or screw action of sufficient strength to prevent entry of moisture into sleeve 13. One particularly suitable device (not shown) is a pair of spring loaded rollers which, as compression takes place rolls slightly backwards, pushing medical material 14 back slightly into sleeve 13 to permit a better seal.

Another possible sealing means (not shown) is a device which pushes the medical material 14 back into the sleeve 13 a sufficient distance (approximately one inch), so that the open end of sleeve 13 may be heat sealed once again.

Figure 3:
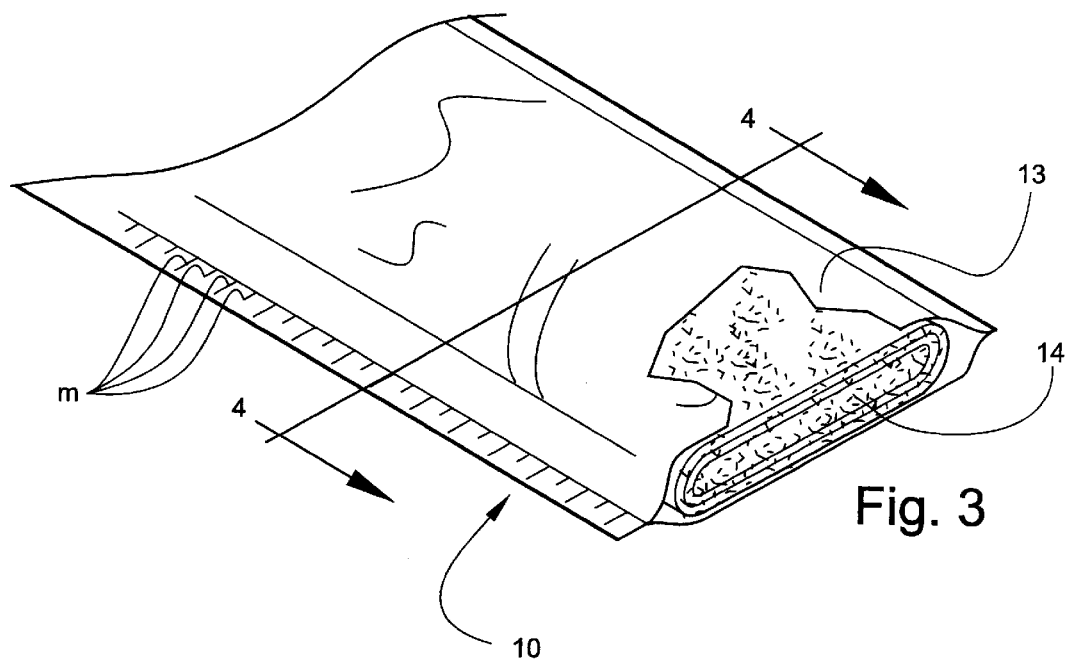
FIG. 3 is a perspective view with parts broken away of a cut length of medical material.

Since the appropriate length of medical material 14 is best determined by measurement, measurement marks "M" may be printed on one edge of the sleeve 13, as is best shown in FIG. 3. Once the appropriate length of medical material 14 has been dispensed and cut from the roll, it is removed from sleeve 13 and sleeve 13 is discarded.

Figure 4:
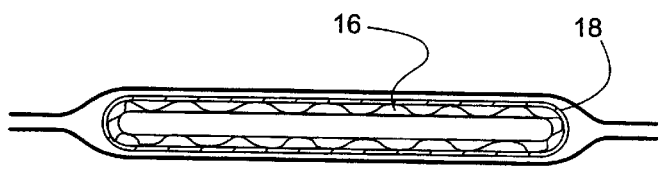
FIG. 4 is a vertical cross-section taken substantially along lines 4—4 of FIG. 3.
Figure 5:
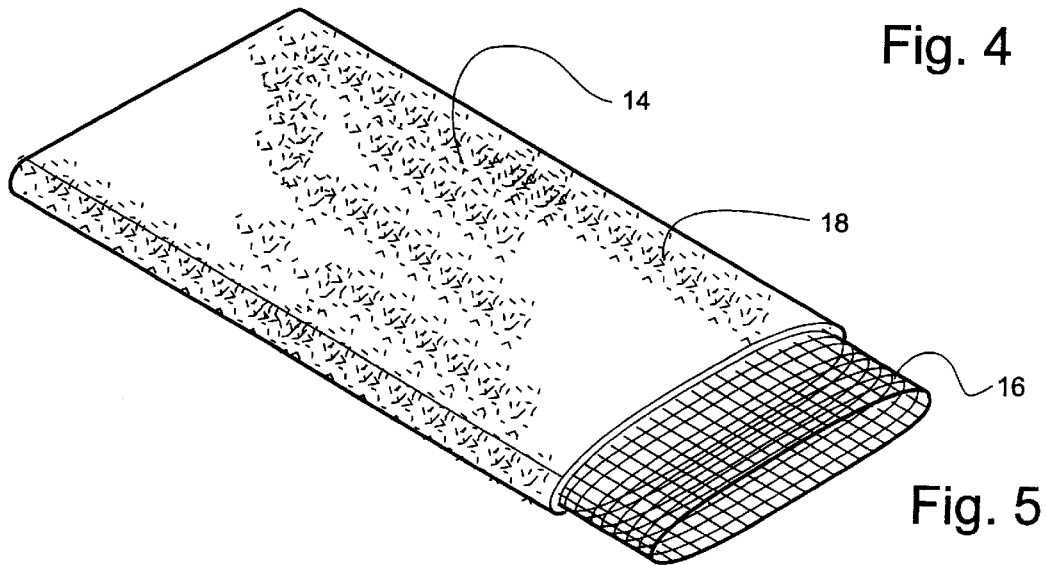
FIG. 5 is a perspective view of a length of the medical material with the substrate layer exposed for clarity.

Referring now to FIGS. 4 and 5, medical material 14 comprises a tubular substrate 16, which is preferably formed by knitting yarns formed of a suitable fiber such as fiberglass into a tube on a circular knitting machine enclosed with a length of tubular wrapping 18. Substrate 16 may alternatively be formed by seaming a length of flat woven or knitted material into a tube with the raw ends of the tube positioned on the inside of the tube by turning the tube inside-out. However, because of the labor involved in these manufacturing steps, knitting the tube is believed to be the most efficient and cost-effective means of forming the substrate. By knitting the substrate 16, the principal remaining construction step is to cut the knitted tube to length so that it generally corresponds to the length of the sleeve 13 into which the prepared medical material 14 will be packaged.

The medical material 14 may be formed in any needed width, for example, between 1 inch and 8 inches. One preferred embodiment comprises a 3 inch wide medical material 14 positioned within a 4 inch wide sleeve 13. In general, the sleeve 13 varies between 3 inches to 10 inches and within that range can accommodate medical material having widths of 1 inch to 8 inches.

A preferred embodiment of the substrate 16 is knitted as a tube on a circular knitting machine, according to the following specifications:

courses 14–19
wales 11–19
yarn specifications DE 37 1/0 Textured Glass

Selection of the particular knitting machine is based on the predetermined specifications for the medical material 14. Variations in the diameter of the medical material 14 can be varied within limits on a particular diameter circular knitting machine by controlling yarn feed and take-up tension, and other variables which are commonplace in the art.

As is shown in FIGS. 6, 7 and 8, substrate is formed by flattening the knitted tube (FIG. 6) to form two major, longitudinally-extending sides 16A, 16B (FIGS. 7 and 8). The flattened tube also forms two opposed, folded side edges 16C, 16D of the substrate 16. In contrast to prior art constructions which include raw, cut edges with a multitude of exposed and outwardly-projecting yarn and fiber ends, these side edges 16C, 16D are rounded, smooth, integral and uncut. Thus, there are no exposed cut ends to harden into sharp, needle-like projections when the curing of the moisture-curable resin is completed. In addition, the substrate is strengthened by the tubular layers acting as a double layer, continuous structure. No sewing is required to align the layers, and the manufacturer has greater control over the width of the medical material 14.

Figure 9:
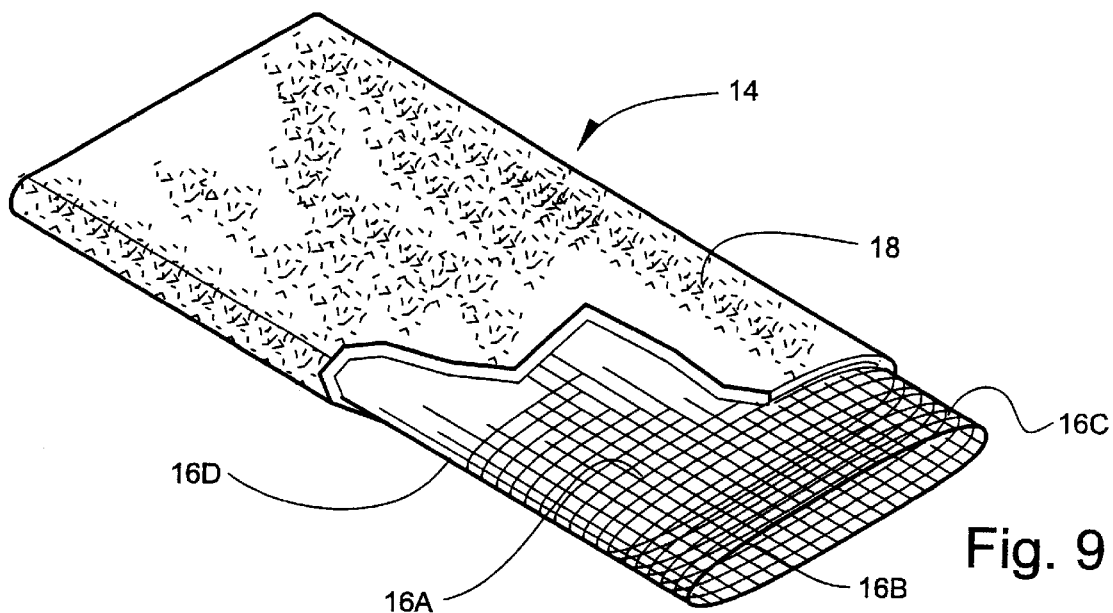
FIG. 9 is a perspective view, with parts broken away, showing the flattened tubular substrate positioned in the padding to form the medical bandage.

A short length of the substrate 16 is shown in FIGS. 6, 7 and 8. Ordinarily, the substrate 16 will be in much longer lengths coextensive with the length of the medical material 14 to be formed. While cut edges are formed on the ends of the substrate 16 when severed from the length of medical material 14, these ends can be folded inwardly and/or covered with a double thickness of the tubular wrapping 18. (See FIG. 9.)

The tubular wrapping 18 is formed of a soft, flexible non-woven fiber such as polypropylene or some other suitable hydrophobic fiber such as is presently used on Ortho-Glass® brand synthetic splinting material manufactured by the Casting Division of Smith & Nephew, Inc., assignee of this application. This product provides a cushioning protective layer between the skin of the patient and hardened substrate 16.

Substrate 16 is impregnated or coated with a reactive system which remains stable when maintained in substantially moisture-free conditions but which hardens upon exposure to sufficient moisture to form a rigid, self-supporting structure. A typical formulation of the reaction system is set forth in the following table:

Typical Formulation

| Typical Formulation: | | |
|---|---|---|
| Isonate↓ 143L or Mondur↓ CD or Rubinate↓ XI168 | polyisocyanate | 50.0% |
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | | 100% |

A complete discussion of the parameters of the reactive system, the manner of production and the variables which apply are found in U.S. Pat. No. 4,411,262.

Figure 10:
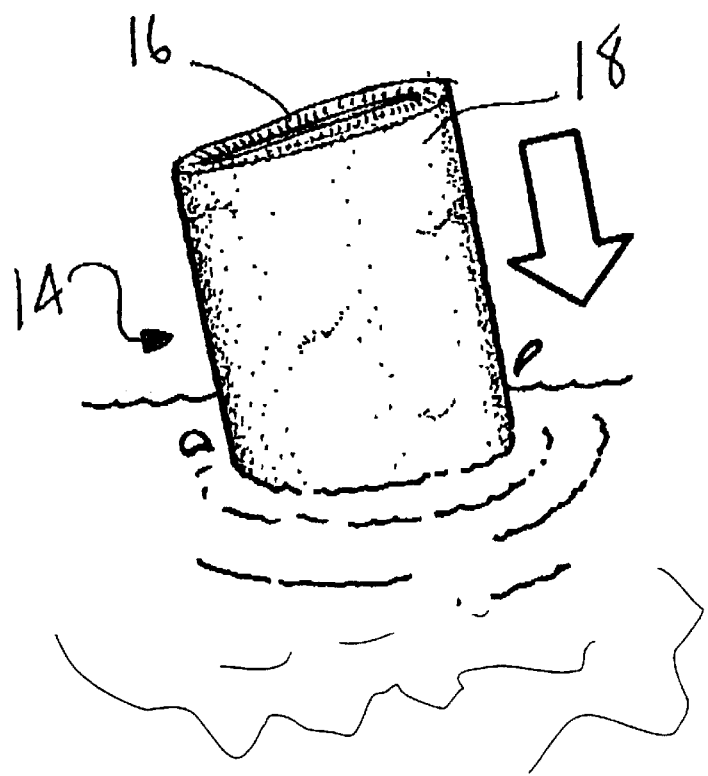
FIG. 10 illustrates the activation of the moisture-curable resin by wetting.

As is shown in FIG. 10, moisture-curing is activated by dipping the medical material 14 in water. Then excess moisture is squeezed from the medical material 14 by, for example, rolling up in a towel.

Alternatively, moisture-curing can take place over a longer period of time by allowing contact between the reactive system on substrate 16 and atmospheric moisture.

Figure 11:
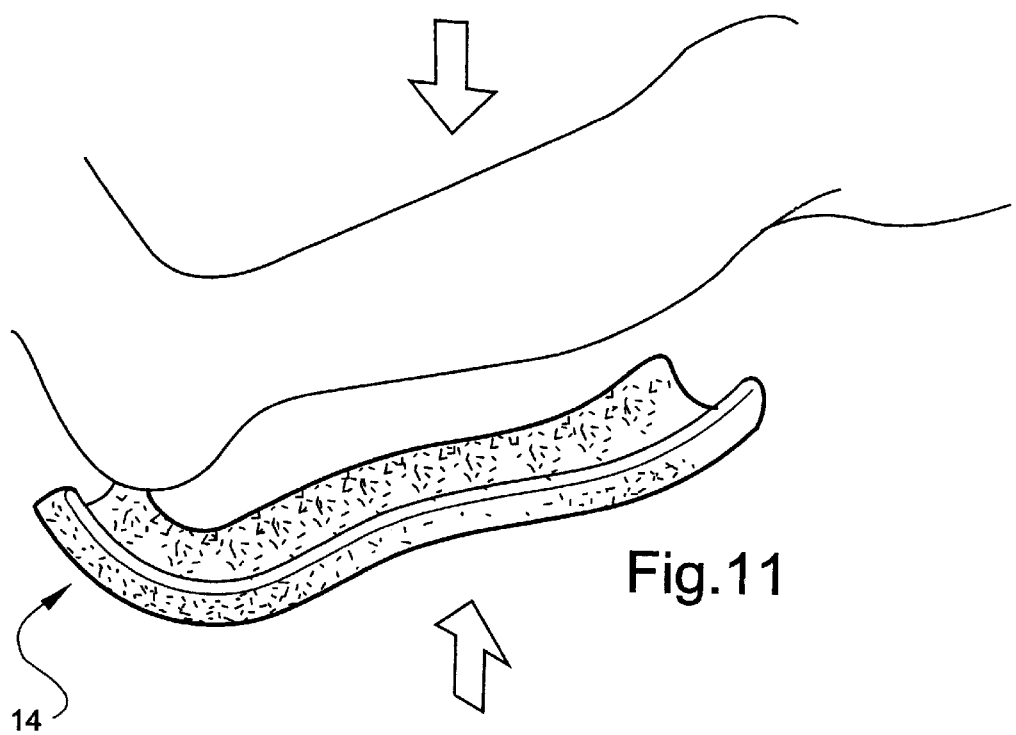
FIG. 11 shows the medical material after removal from the sleeve being formed to fit the contour of a body member.
Figure 12:
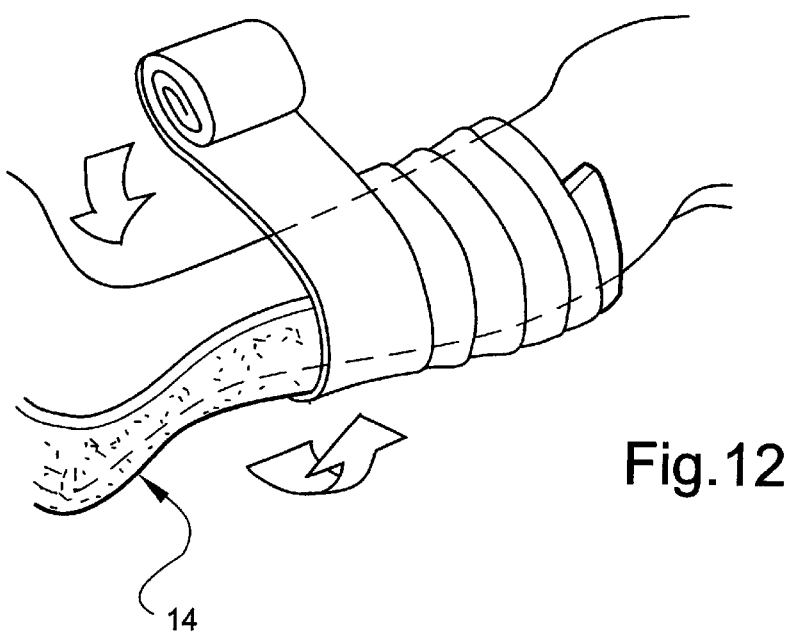
FIG. 12 is a perspective view of the hardening medical material being secured into place on a body member by means of a covering wrap.

Referring now to FIG. 11, an appropriate length of the medical material 14 is formed to the shape of the body member to be immobilized. This particular type of splint, known as a posterior short leg splint, is formed by molding a length of the medical material 14 to the calf and up over the heel and onto the foot. Then, medical material 14 is overwrapped with an conventional elastic bandage, as is shown in FIG. 12.

Figure 13:
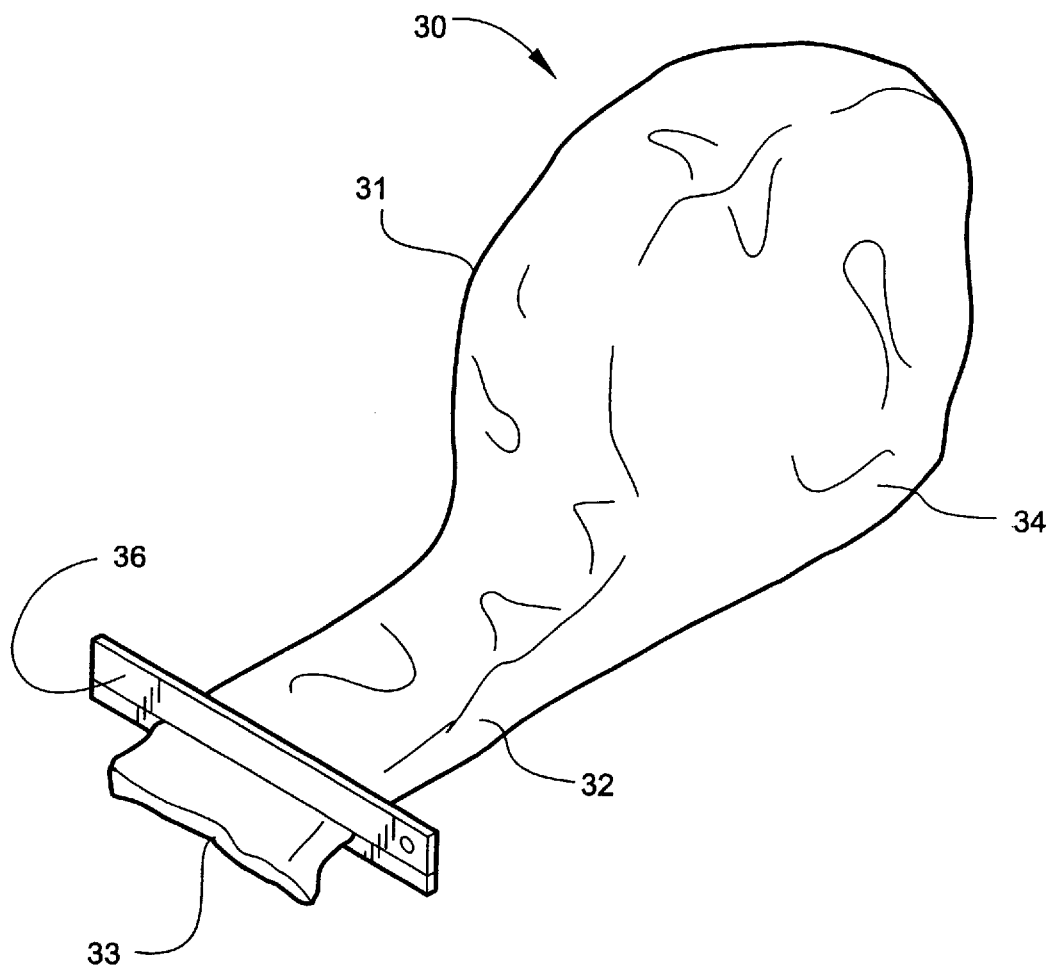
FIG. 13 is a perspective view of a dispensing container for holding the medical material according to an alternative embodiment.

Referring now to FIG. 13, medical bandaging product according to another embodiment of the invention is shown at broad reference numeral 30. The medical material 14 is positioned within a container 31 which is formed of two laminated sheets placed in registration and heat-sealed along a common seam to form a moisture-proof container of the same material and construction as the sleeve 13. The outer layer is formed of a tear-resistant plastic film and the middle layer comprises aluminum foil and acts as a moisture barrier. The inner layer is a plastic film having thermoplastic properties suitable for heat sealing the interior of container 31 securely against intrusion of moisture.

As is also shown in FIG. 11, container 31 comprises an elongate dispensing sleeve 32 having an openable end 33 through which the medical material 14 in the container 31 is dispensed. A coil of the medical material 14 is positioned in an enlarged product storage package 34 which is integral and communicates with dispensing sleeve 32.

The end 33 of dispensing sleeve 32 may be sealed with a clamp 36 of any suitable type, for example, the clamp 36 described above, or a "zip-lock"-type integrally-formed zipper of a type which is typical on sandwich bags and other food storage bags.

Figure 14:
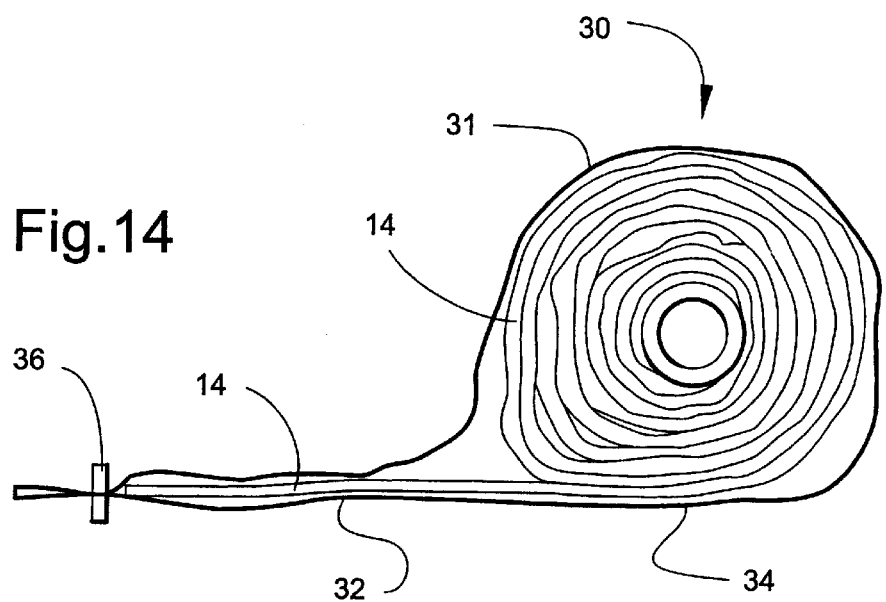
FIG. 14 is a vertical side elevation with partial cross-section of the dispensing container shown in FIG. 13.

As is shown in FIG. 14, dispensing sleeve 32 fits snugly around the medical material 14 in order to limit exposure of the medical material 14 to air which enters when the opening 33 is not sealed. FIG. 14 also illustrates that the medical material 14 is coiled into a relatively tight coil that limits exposure to air of the medical material 14 remaining in the container 31. When opening 33 is properly sealed, container 31 is sufficiently airtight so that medical material 14 remains in its soft, uncured state for much longer that the usual length of time needed to exhaust the supply of medical material 14 in container 31. If a short length of the medical material 14 adjacent the opening 33 should happen to harden, it can be cut away and discarded.

A desired length of medical material 14 is dispensed by removing clamp 36 and grasping the exposed end of the medical material 14. The appropriate length is pulled out of container 31—the medical material 14 uncoiling in the storage package 34. When the proper length has been dispensed through opening 33, it is cut and the end of the medical material 14 remaining in the container 31 is tucked back into the dispensing sleeve 32. The open end 33 is quickly resealed with the clamp 36.

Figure 15:
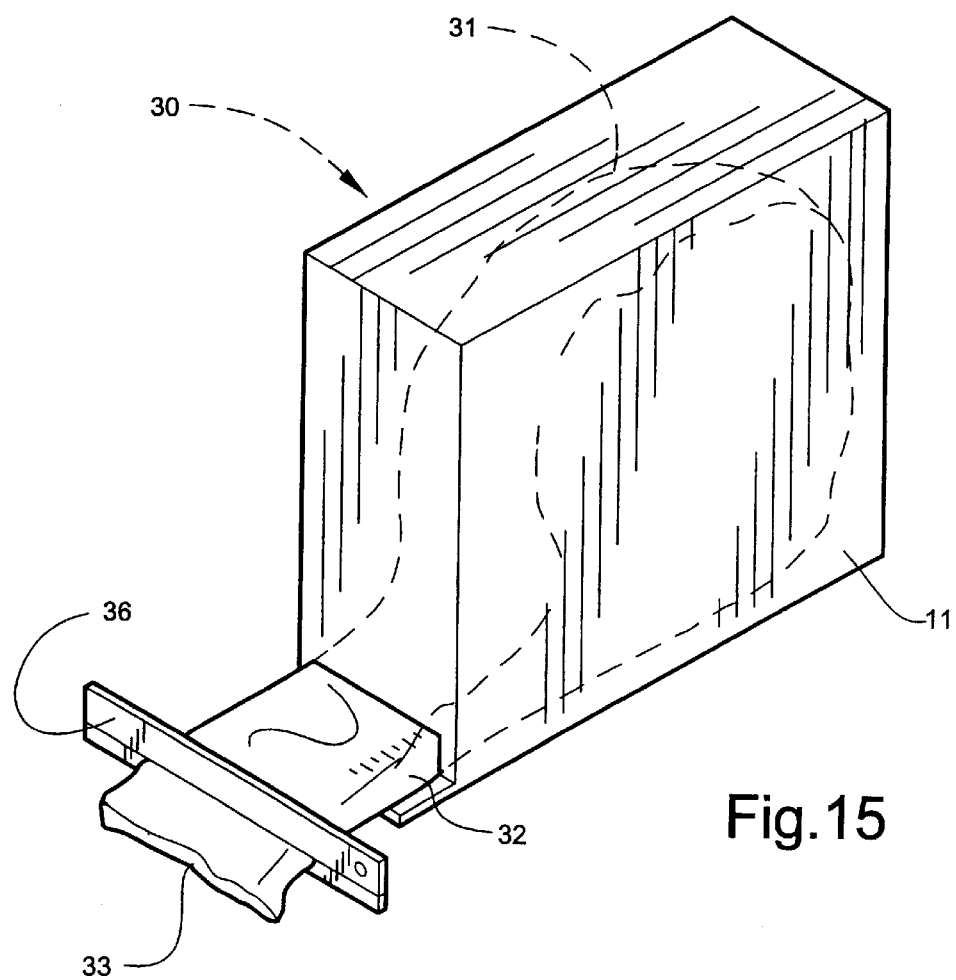
FIG. 15 is a perspective view of carton into which the dispensing container, also shown, is positioned.

As is shown in FIG. 15, the medical bandaging product 30 can be placed inside a dispensing carton 11, with the dispensing sleeve 32 of container 31 projecting out of the slot in the bottom of carton 11.

A medical bandaging product is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. An elongate medical bandaging product for being dispensed in lengths suitable for application in a flattened state to at least one aspect of a body part to be protected, comprising:
   (a) an elongate sleeve of a predetermined length formed of a moisture-impervious material and sealable to prevent entry of moisture;
   (b) an elongate medical material having substantially the same predetermined length as said elongate sleeve and positioned in a continuous layer which coextends within the sleeve in substantially moisture-free conditions and sealed therein against moisture until use, said medical material comprising:
      (i) a flattened tubular substrate having a pair of opposed, major surfaces defining folded side edges extending along the length of the elongate sleeve and characterized by being substantially free of cut fibrous ends;
      (ii) a reactive system impregnated into or coated onto said flattened tubular substrate, said system remaining stable when maintained in substantially moisture-free conditions and hardening upon exposure to sufficient moisture to form a rigid, self supporting structure; and
      (iii) a soft, flexible protective wrapping enclosing said flattened substrate along its length to provide a cushioning barrier between the substrate and the skin of a patient when the material is in use;
   whereby a desired length of said medical material is removable from the length of bandaging product by severing the medical material and the sleeve at a desired point without removing additional excess medical material from the sleeve whereby the sleeve and medical material form a continuum of elongate bandaging product and whereby said sleeve is sealable against entry of moisture after a desired length of said medical material has been dispensed for use to prevent hardening of said substrate remaining in said sleeve.

2. A medical bandaging product according to claim 1, wherein said tubular substrate comprises a knitted fabric.

3. A medical bandaging product according to claim 1, wherein said tubular substrate comprises a seamless knitted fabric knitted on a circular knitting machine.

4. A medical bandaging product according to claim 1, wherein said tubular substrate comprises a knitted fabric knitted on a flat knitting machine having a seam therein which binds two side edges of the knitted fabric together to form a tube.

5. A medical bandaging product according to claim 1, 2, 3 or 4, wherein said sleeve comprises a aluminum foil laminate having an outer tear resistant layer, a central aluminum foil layer and an inner heat sealable plastic layer.

6. A medical bandaging product according to claim 5, wherein said tubular substrate is formed of fibers selected from the group consisting of fiberglass and synthetic thermoplastic fibers.

7. A medical bandaging product according to claim 5, wherein said protective wrapping enclosing the substrate comprises a fibrous nonwoven cushion.

8. A medical bandaging product according to claim 5, wherein said protective wrapping enclosing the substrate comprises a nonwoven polypropylene tube.

9. A medical bandaging product according to claim 5, wherein said reactive system comprises a blended polyisocyanate, polyol, catalyst and stabilizer.

10. A medical bandaging product according to claim 5, wherein said sleeve is formed into a coil.

11. A medical bandaging product according to claim 10, and including a dispensing carton within which the coil of medical banding product is contained.

12. A medical bandage according to claim 5, wherein said medical bandage is formed into a coil.

13. A medical bandage according to claim 12, and including a dispensing carton within which the coil of medical bandaging product is contained.

14. An elongate medical bandage for application in a flattened state to at least one aspect of a body part to be protected, comprising:
   (a) an elongate medical material adapted for being maintained in substantially moisture-free conditions until use, said medical bandage comprising:
      (i) a flattened tubular substrate defining a pair of opposed major surfaces defining folded side edges extending along the length of the substrate and characterized by being substantially free of cut fibrous ends;
      (ii) a reactive system impregnated into or coated onto said flattened substrate, said system remaining stable when maintained in substantially moisture-free conditions and hardening upon exposure to sufficient moisture to form a rigid, self supporting structure; and
      (iii) a soft, flexible protective wrapping enclosing said flattened substrate along its length to provide a cushioning barrier between the substrate and the skin of a patient when the bandage is in use.

15. A medical bandage according to claim 14, wherein said tubular substrate comprises a knitted fabric.

16. A medical bandage according to claim 14, wherein said tubular substrate comprises a seamless knitted fabric knitted on a circular knitting machine.

17. A medical bandage according to claim 14, wherein said tubular substrate comprises a knitted fabric knitted on a flat knitting machine having a seam therein which binds two side edges of the knitted fabric together to form a tube.

18. A medical bandage according to claim 14, 15, 16, or 17, wherein medical bandage is packaged until use in a sleeve comprising an aluminum foil laminate having an outer tear resistant layer, a central aluminum foil layer and an inner heat sealable plastic layer.

19. A medical bandage according to claim 18, wherein said tubular substrate is formed of fibers selected from the group consisting of fiberglass and synthetic thermoplastic fibers.

20. A medical bandage according to claim 18, wherein said protective wrapping enclosing the substrate comprises a fibrous nonwoven cushion.

21. A medical bandage according to claim 18, wherein said protective wrapping enclosing the substrate comprises a nonwoven polypropylene tube.

22. A medical bandage according to claim 18, wherein said reactive system comprises a blended polyisocyanate, polyol, catalyst and stabilizer.

23. A medical bandage according to claim 14, wherein said soft, flexible protective wrapping enclosing said substrate comprises freely water and air permeable through the thickness thereof for providing a cushioning barrier between the substrate and the skin of a patient when the bandage is in use, and which permits the moisture-curable resin to be quickly and easily exposed to water through the thickness thereof.

24. A medical bandage according to claim 14, wherein said soft, flexible, protective wrapping surrounds the substrate so that either of the enclosed major surfaces of the substrate may be placed adjacent the skin of the patient.

25. An elongate medical bandaging product for being dispensed in lengths suitable application in a flattened state to at least one aspect of a body part to be protected, comprising:

(a) an outer container formed of a moisture-impervious material and sealable to prevent entry of moisture, the container comprising an elongate product-dispensing sleeve having a moisture-proof sealable opening on one end and an enlarged product storage package communicating with the dispensing sleeve;

(b) an elongate medical material positioned in the container in substantially moisture-free conditions and sealed therein against moisture until use, said medical material comprising:

(i) a flattened tubular substrate having a pair of opposed, major surfaces defining folded side edges extending along the length of the elongate sleeve and characterized by being substantially free of cut fibrous ends;

(ii) a reactive system impregnated into or coated onto said flattened substrate, said system remaining stable when maintained in substantially moisture-free conditions and hardening upon exposure to sufficient moisture to form a rigid, self supporting structure;

(iii) a soft, flexible protective wrapping enclosing said flattened substrate along its length to provide a cushioning barrier between the substrate and the skin of a patient when the material is in use; and (c) closure means for resealing the dispensing sleeve against entry of moisture after a predetermined length of the medical material has been dispensed for use to prevent hardening of the substrate remaining in the product container.

26. A medical bandaging product to claim 25, wherein said dispensing sleeve and said product storage package are integrally-formed.

27. A medical bandaging product to claim 25, and including a protective carton within which said product container is contained.

28. A medical bandaging product according to claim 25, 26 or 27, and wherein said elongate medical material is coiled within said storage package with an end portion thereof positioned in said product-dispensing sleeve for selective dispensing of desired lengths thereof.

29. An elongate medical bandaging product for being dispensed in lengths suitable for application in a flattened state to at least one aspect of a body part to be protected, comprising:

(a) an elongate sleeve of a predetermined length formed of a moisture-impervious material and sealable to prevent entry of moisture;

(b) an elongate medical material having substantially the same predetermined length as said elongate sleeve and positioned in a continuous layer which coextends within the sleeve in substantially moisture-free conditions and sealed therein against moisture until use, said medical material comprising:

(i) a flattened tubular substrate having a pair of opposed, major surfaces defining folded side edges extending along the length of the elongate sleeve and characterized by being substantially free of cut fibrous ends; and (ii) a reactive system impregnated into or coated onto said flattened tubular substrate, said system remaining stable when maintained in substantially moisture-free conditions and hardening upon exposure to sufficient moisture to form a rigid, self supporting structure;

whereby a desired length of said medical material is removable from the length of bandaging product by severing the medical material and the sleeve at a desired point without removing additional excess medical material from the sleeve whereby the sleeve and medical material form a continuum of elongate bandaging product and whereby said sleeve is sealable against entry of moisture after a desired length of said medical material has been dispensed for use to prevent hardening of said substrate remaining in said sleeve.

30. An elongate medical bandage for application in a flattened state to at least one aspect of a body part to be protected, comprising:

(a) an elongate medical material adapted for being maintained in substantially moisture-free conditions until use, said medical bandage comprising:

(i) a flattened tubular substrate defining a pair of opposed major surfaces defining folded side edges extending along the length of the substrate and characterized by being substantially free of cut fibrous ends; and (ii) a reactive system impregnated into or coated onto said flattened substrate, said system remaining stable when maintained in substantially moisture-free conditions and hardening upon exposure to sufficient moisture to form a rigid, self supporting structure.

31. An elongate medical bandaging product for being dispensed in lengths suitable for application in a flattened state to at least one aspect of a body part to be protected, comprising:

(a) an outer container formed of a moisture-impervious material and sealable to prevent entry of moisture, the container comprising an elongate product-dispensing sleeve having a moisture-proof sealable opening on one end and an enlarged product storage package communicating with the dispensing sleeve;

(b) an elongate medical material positioned in the container in substantially moisture-free conditions and sealed therein against moisture until use, said medical material comprising:

(i) a flattened tubular substrate having a pair of opposed, major surfaces defining folded side edges extending along the length of the elongate sleeve and characterized by being substantially free of cut fibrous ends;

(ii) a reactive system impregnated into or coated onto said flattened substrate, said system remaining stable when maintained in substantially moisture-free conditions and hardening upon exposure to sufficient moisture to form a rigid, self supporting structure;

(iii) a soft, flexible protective wrapping enclosing said flattened substrate along its length to provide a cushioning barrier between the substrate and the skin of a patient when the material is in use; and (c) closure means for resealing the dispensing sleeve against entry of moisture after a predetermined length of the medical material has been dispensed for use to prevent hardening of the substrate remaining in the product container.

\* \* \* \* \*